United States Patent [19]

Asher

[11] 4,183,962
[45] Jan. 15, 1980

[54] PROCESS FOR OXYGENATING BLOOD BY THE UTILIZATION OF LIQUID MEMBRANES

[75] Inventor: William J. Asher, Fanwood, N.J.

[73] Assignee: Exxon Research & Engineering Co., Florham Park, N.J.

[21] Appl. No.: 869,838

[22] Filed: Jan. 16, 1978

[51] Int. Cl.² .................. A61K 45/00; A61K 31/02; A61K 31/025
[52] U.S. Cl. ........................ 424/366; 435/2; 424/101; 424/350; 424/352
[58] Field of Search ............... 424/350, 352, 366, 101; 195/1.8

[56] References Cited

U.S. PATENT DOCUMENTS

| | | | |
|---|---|---|---|
| 3,733,776 | 5/1973 | Li et al. | 195/1.8 |
| 3,962,439 | 6/1976 | Yokoyama et al. | 424/352 |
| 3,989,843 | 11/1976 | Chabert et al. | 424/352 |

*Primary Examiner*—Sam Rosen

*Attorney, Agent, or Firm*—E. A. Forzano; Joseph J. Allocca

[57] ABSTRACT

The instant invention relates to an improved process for oxygenating blood comprising: contacting said blood with oxygen-containing bubbles, said bubbles being coated with a liquid membrane, said liquid membrane phase permitting the permeation of oxygen into the blood whereby at least a portion of said oxygen passes through said membrane and into said blood; removing said liquid membrane coated bubbles as a three phase foam comprising gas bubbles coated with said liquid membrane suspended in blood; and coalescing said foam comprising gas bubbbles to form three separate bulk phases comprising the liquid membrane phase, a gaseous phase and a blood phase, wherein the improvement comprises a liquid membrane phase comprising a biologically non-retainable liquid halocarbon compound. These liquid membrane formulations having a membrane phase comprising a biologically non-retainable liquid halocarbon compound exhibit improved coalescing characteristics.

14 Claims, No Drawings

4,183,962

PROCESS FOR OXYGENATING BLOOD BY THE UTILIZATION OF LIQUID MEMBRANES

BRIEF DESCRIPTION OF THE INVENTION

The instant invention relates to a process for oxygenating mammalian and preferably human blood while simultaneously removing carbon dioxide from the blood. More particularly, this invention pertains to a process for oxygenating human blood and removing carbon dioxide from such blood by contacting the blood with oxygen-containing gas bubbles; said bubbles are coated with a liquid membrane which isolates blood from the gaseous oxygen. Said liquid membrane-containing gaseous bubbles travel through the blood and form a three phase foam which comprises a blood suspending phase, a liquid membrane exterior phase and a gaseous interior phase.

The instant invention comprises an improved process for coalescing said three phase foam by removing said foam from the bulk off the blood phase and coalescing said foam into the membrane phase, the gaseous phase and blood phase, wherein the improvement comprises a membrane phase comprising a biologically non-retainable liquid halocarbon compound or mixtures of said liquid halocarbon compounds.

SUMMARY OF THE PRIOR ART

U.S. Pat. No. 3,733,776, Norman N. Li and William J. Asher, inventors, entitled, Liquid Membrane Artificial Lung, broadly discloses the use of liquid fluorocarbons as the membrane phase in the liquid membrane oxygenating process. This patent does not discuss the coalescing characteristics of the liquid membrane compositions described herein. In fact, at column 4, lines 1 to 5, the patent teaches the compounds preferred as membrane phase components, i.e. fluorocarbons containing heteroatoms such as oxygen and nitrogen, are herein demonstrated to have undesirable coalescing characteristics and, therefore, not desirable components of a membrane phase for blood oxygenation.

It has been discovered that the accumulation with time of a stable emulsion of fluorocarbon and blood components occurs in the settling chamber during the liquid membrane oxygenation process of U.S. Pat. No. 3,733,776. The accumulation of a stable emulsion of the membrane phase and blood components in the collapse chamber of a liquid membrane oxygenator is undesirable in three ways:

(1) volume has to be provided in the collapse chamber to contain the emulsion;

(2) the location of the accumulated emulsion must be controlled to prevent it from disturbing the steams exiting from the collapse chamber; and (3) additional membrane phase must be added to the device with time to replace the membrane phase incorporated in the emulsion remaining in the collapse chamber. All of these characteristics decrease the desirability of using the liquid membrane blood oxygenator, so substantial elimination of all three is a considerable practical advantage. The practice of the instant invention results in improved coalescence after blood contact with the liquid membrane composition reducing the above disadvantages. Such improved coalescence can be achieved by the utilization of a biologically non-retainable liquid halocarbon compound as a component in the membrane phase.

There is no reference in the prior art suggesting this characteristic of liquid halocarbons when they are utilized as liquid membrane components. Demulsification by the use of solid fluorocarbons is fairly well-known in the art. Three examples of this include U.S. Pat. No. 3,098,108, A. Preiser, Coalescing Sulfuric Acid-Hydrocarbon Emulsions; U.S. Pat. No. 3,235,611, Gaines C. Jeffrey, Telomers of Tetrafluoroethylene and Tetrachloroethylene; U.S. Pat. No. 3,405,059, Frank B. Sprow, Settling of Emulsions. These fluorocarbons are kept separate from the emulsion compositions and are contacted with these emulsions only to demulsify them. There is no suggestion that a halocarbon can be utilized to form an emulsion with the characteristics disclosed herein.

DETAILED DESCRIPTION OF THE INVENTION

It has been unexpectedly discovered that the utilization of liquid halocarbons as the liquid membrane phase of the liquid membrane process for oxygenating blood, displays improved coalescing characteristics over the fluorocarbons presently preferred by the prior art. Broadly, the membrane phase comprises a biologically non-retainable liquid halocarbon compound or a mixture of said halocarbon compounds. Preferably, the membrane phase comprises one biologically non-retainable liquid halocarbon compound; more preferably the membrane phase consists of a biologically non-retainable liquid halocarbon compound or a mixture of said halocarbon compounds; and most preferably, the membrane phase consists of one biologically non-retainable liquid halocarbon compound.

These halocarbons are those which contain solely carbons and halogens, preferably the halogens are fluorine and bromine, and do not contain other heteroatoms such as oxygen nitrogen and hydrogen.

It has been determined that halocarbons that are not substantially biologically retained by the mammalian system oxygenated by this liquid membrane process have improved coalescing characteristics over the fluorocarbons presently preferred by the prior art which are substantially biologically retained under the same conditions. The preferred compositions found to exhibit this biological non-retainable characteristic are fluorocarbons, i.e. the composition contains solely carbon and fluorine and no other chemical species. These compounds can range from $C_6$ to $C_{25}$, preferably $C_7$ to $C_{15}$, and most preferably from $C_8$ to $C_{12}$. Preferably these fluorocarbons contain only saturated carbon atoms, i.e. no olefinic $C=C$ double bonds and no aromatic rings. These fluorocarbons can be straight chained, branched chain or cyclic. The cyclic configuration is preferred, however. Fluorocarbons may be substituted with chlorine and bromine, preferably bromine, such as in perfluorooctylbromide. The fluorocarbons without such substitution are the preferable species in the process of the instant invention.

The most preferred fluorocarbons are selected from the group consisting of perfluorodecaline

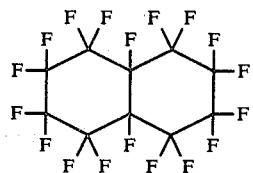

(which is marketed by I.S.C. Chemicals Limited of England under the tradename of PP-5), and perfluoromethyldecaline

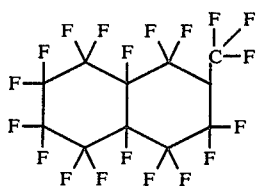

(marketed by I.S.C. Chemicals Limited of England under the trandename of PP-9).

It is also possible to formulate liquid membrane exterior phases possessing improved coalescing characteristics with mixtures of compositions fitting the above description. These mixtures are not the preferred embodiments, however.

There are a number of techniques that may be employed to determine the biological retainability of a given halocarbon. One method is described below. Those skilled in the art will be able to devise equivalent procedures.

A halocarbon is defined as biologically non-retainable if at least 50% of said halocarbon introduced into the treated animal through this blood oxygenation process is eliminated from the treated animal after four months. Preferably, at least 75% is eliminated in two months. As noted above, the treated animal may be a mammal, preferably human. A simple test to determine biological retainability, using a representative test animal such as a rat or mouse, is presented below. Those skilled in the art can devise equivalent procedures.

The halocarbon to be tested is emulsified as the dispersed phase in an aqueous medium of physiologic osmolarity. The medium is preferably blood plasma. The droplet size of halocarbon is less than 1μ and preferably less than 0.1μ. A typical emulsion would be 10% by volume fluorocarbon/plasma and be no greater than 50% by volume of normal blood volume of the test animal. This emulsion is then administered intravenously to test animals, preferably rats or mice. The amount retained is determined on sacrifice of the animal by whole body analysis, or analysis of the liver and lungs of the liver alone since those skilled in the art believe the halocarbons concentrate in those organs. The quantities of retained halocarbon from any of the above tests should be nearly equivalent and under 50% after four months and preferably 25 percent after two months for acceptable halocarbons. In all the tests for retained halocarbons, standard biological procedures such as homogenization of the tissue followed by hexane extraction and chemical analysis of the extract by standard chemical means for the fluorine content of the halocarbon can be used.

Halocarbons substantially eliminated from the body of the test animal after the introduction of the halocarbon into the cardiovascular system of the test animal, as described above, will exhibit improved coalescing characteristics when utilized as the membrane phase in a liquid membrane oxygenating process. As defined above, substantial elimination from the test animal is defined as the elimination from a test animal of 50% halocarbon in a fine particle emulsion, as defined above, intravenously administered within 4 months and preferably the elimination of 75% of that halocarbon in two months. Similarly, a non-biologically retained halocarbon is defined as one which after administration intravenously as a fine particle emulsion is 75 percent or more eliminated from the test animal in two months.

The liquid membrane-containing gaseous bubbles of oxygen suspended in the blood phase, may be formed by conventional methods under the conditions utilized in the prior art liquid membrane oxygenation processes. Methods for forming and utilizing these liquid membrane formulations are summarized below. U.S. Pat. No. 3,733,776, Norman N. Li and William J. Asher, inventors, referred to above, is hereby incorporated by reference as a reference to the practitioner for the details of these conventional techiques. The ratio of membrane phase to interior phase using the membrane phases described herein has a range similar to the other oxygenation compositions using fluorocarbons in the prior art. The preferred ranges of composition make-up with the instant invention are disclosed in copending application Ser. No. 869,836, Single Shell Liquid Membrane Formulations Having Improved Stability and Methods for Preparing and Using Said Formulations, W. J. Asher, inventor, which is hereby incorporated by reference.

The liquid membrane coated gaseous bubbles can be formed by either bubbling the oxygen-containing gas through the membrane phase comprising the biologically non-absorbable halocarbon. The gaseous bubbles are allowed to move through the membrane phase to the blood phase. Here the bubbles move through the blood phase carrying a liquid membrane surrounding the bubble. The liquid membrane encapsulated droplets tend to move up because of their low density countercurrent to the downward flow of blood forming a foam settling at the upper part of the contact chamber. However, concurrent flow of encapsulated bubbles and blood may be used by simply using blood velocities in the device greater than the rise velocities of the liquid membrane encapsulated bubbles being utilized.

This foam is then removed from the bulk of the blood phase in a primary oxygenation zone by such conventional techniques as displacement over a weir or dam to a separate zone or vessel, and allowed to coalesce with time. This displacement can, of course, be simply achieved by having the flows into the primary oxygenation zone (which is a closed chamber except for the path over the dam or weir) exceed the flows withdrawn by all paths except the path over the dam or weir. A separate vessel is normally provided for the coalescing of the foam which allows the collection of the halocarbon from the liquid membranes in a zone of low blood flow rate so that drops of halocarbon are not axmixed with the blood, something that should be avoided.

This liquid membrane-containing foam removed from the bulk of the blood phase is allowed to coalesce with little or no agitation. Gentle stirring or passage of the foam through coalescing screens may be used as an aid to coalescing the foam but are not required, however.

Four phases tend to form in the coalescing chamber. The top phase is the spent gas from the oxygenation which has reduced oxygen content and enhanced carbon dioxide content. This gas may be vented. Below the gas phase is the three phase foam. This three phase foam isolates a blood phase collecting below it from the potentially damaging gas phase. This quantity of blood using conventional operating procedures will be very small in comparison to the quantity of blood oxygenated in the primary oxygenation zone. This blood which is oxygenated has been protected from a blood-gas interface so that it may be recirculated to the patient. The lowest phase is the halocarbon phase which can be recycled and used to make liquid membranes again. Between the blood-halocarbon interface may form a blood-halocarbon compostion formed by the chemical interaction of the blood and the halocarbon during contact in the oxygenating chamber. This composition is usually a semi-solid or viscous liquid which can be separated from the other phases by filtration or other conventional methods.

The following example is presented to illustrate and not limit the instant invention.

EXAMPLE 1

Five fluorocarbons were compared for coalescing characteristics. The Liquid Membrane Generator, W. J. Asher and H. C. Tsien, inventors, subject of copending application Ser. No. 869,837 was utilized to make each liquid membrane formulation. Briefly, this liquid membrane generator formed the liquid membranes as follows. Gaseous oxygen (205 ml/minute) was passed through a porous layer into the fluorocarbon liquid membrane phase so that it was dispersed therein. The fluorocarbon was supplied to this dispersion chamber at the rate of 0.75 ml/minute for each test run. The dispersion was passed through a perforated outlet zone into the plasma phase so as to form the liquid membrane coated bubbles of gaseous oxygen suspended in the plasma phase of about 1000$\mu$ in diameter. For each test run, the liquid membranes were formed and contacted in a column above the generator with the plasma phase at ambient temperature and pressure for five hours. The three phase foam was displaced from the top of the column with additional plasma flowing into the column near the top. The collapse chamber utilized gravity to coalesce the three phase foam and any emulsion which formed under these conditions was allowed to accumulate at the plasma-fluorocarbon interface. At the end of each run, the amount of accumulated emulsion was measured and is compared in Table I.

TABLE I

Coalescing Characteristics Of Different Fluorocarbon Liquid Membrane Formulations

| Liquid Membrane Phase | Unsettled Emulsion (gm) |
| --- | --- |
| 10 wt. % 11-21[1] in E-4[3] | 155 ± 48 (standard deviation) |
| FC-47[2] | 76. |
| E-4[3] | 70. |
| FC-80[4] | 23.5 ± 13.0 (standard deviation) |
| PP-9[5] | 1.0 |

[1] 11-21 is tradename or code of a polychlorotrifluoroethylene with a viscosity about 64 centipoises at body temperature. It is manufactured by Halocarbon Products Corp. of Hackensack, N.J.
[2] FC-47 is $(C_4F_9)_3N$, perfluortributylamine. It is manufactured by 3M Company, Saint Paul, Minnesota.
[3] E-4 is the trade designation of
$F(CFCF_2O)_4CHFCF_3$
  |
 $CF_3$
manufactured by E.I. duPont Nemours and Company, Wilmington, Delaware.
[4] FC-80 is the trade designation of $C_8F_{16}O$, perfluortetrahydrobutylfuran. It is manufactured by 3M Company, Saint Paul, Minnesota.
[5] PP-9 (defined in text)

From Table I, it can be seen tht PP-9, the fluorocarbon containing only fluorine and carbon had accumulated only one gram of emulsion. Each of the other fluorocarbon liquid membrane formulations tested contained a heteroatom such as oxygen or nitrogen. Each of these formulations had accumulated anywhere from 23 times to 155 times more emulsion during the coalescence of the three phase foam. Clearly, the PP-9 displayed superior coalescing characteristics.

What is claimed is:

1. An improved process for oxygenating blood comprising contacting said blood with gaseous oxygen-containing bubbles, said bubbles being coated with a liquid membrane, said liquid membrane permitting the permeation of oxygen into the blood whereby at least a portion of said oxygen passes through said membrane and into said blood; removing said liquid membrane coated bubbles as a three phase foam comprising gas bubbles coated with said liquid membrane suspended in blood; and coalescing said foam comprising gas bubbles to form three separate bulk phases comprising the liquid membrane phase, a gaseous phase and a blood phase, wherein the improvement comprises a liquid membrane phase comprising a biologically non-retainable $C_6$-$C_{25}$ liquid per-halocarbon compound or a mixture of biologically non-retainable liquid per-halocarbon compounds, wherein at least 50% of any of said per-halocarbon which may be introduced into the treated animal by said process is eliminated from the treated animal after four months.

2. The process of claim 1 wherein at least 75% of said per-halocarbon present after treatment of said blood is eliminated from the treated animal after two months.

3. The process of claim 1 wherein said liquid membrane comprises one biologically non-retainable liquid per-halocarbon compound.

4. The process of claim 2 wherein said per-halocarbon is substituted with a halogen selected from the group consisting of fluorine, chlorine and bromine.

5. The process of claim 2 wherein said per-halocarbon is substituted with a halogen selected from the group consisting of fluorine and bromine.

6. The process of claim 2 wherein said per-halocarbon is substituted solely with fluorine.

7. The process of claim 6 wherein said per-halocarbon compound is selected from the group consisting of straight chain, branched chain or cyclic halocarbons containing from 6 to 25 carbon atoms per molecule wherein each of said carbon atoms is saturated.

8. The process of claim 7 wherein said per-halocarbon compound is cyclic.

9. The process of claim 6 wherein said per-halocarbon compound is selected from the group consisting of straight chain, branched chain or cyclic halocarbons containing from 7 carbons to 15 carbons wherein each of said carbons is saturated.

10. The process of claim 9 wherein said per-halocarbon compound is cyclic.

11. The process of claim 6 wherein said per-halocarbon compound is selected from the group consisting of straight chain, branched chain or cyclic halocarbons containing from 8 carbons to 12 carbons wherein each of said carbons is saturated.

12. The process of claim 11 wherein said per-halocarbon compound is cyclic.

13. The process of claim 2 wherein said per-halocarbon is selected from the group consisting of perfluorooctylbromide, perfluorodecaline and perfluoromethyldecaline.

14. The process of claim 2 wherein said per-halocarbon compound is selected from the group consisting of perfluorodecaline and perfluoromethyldecaline.

* * * * *